United States Patent [19]

Tedder

[11] Patent Number: 5,215,902

[45] Date of Patent: * Jun. 1, 1993

[54] PROCESS FOR RECOVERING ALCOHOL WITH ENERGY INTEGRATION

[75] Inventor: Daniel W. Tedder, Marietta, Ga.

[73] Assignee: Georgia Tech Research Corporation, Atlanta, Ga.

[*] Notice: The portion of the term of this patent subsequent to Jul. 30, 2008 has been disclaimed.

[21] Appl. No.: 623,537

[22] Filed: Dec. 7, 1990

Related U.S. Application Data

[63] Continuation-in-part of Ser. No. 298,216, Jan. 17, 1989, Pat. No. 5,036,005, which is a continuation-in-part of Ser. No. 54,037, May 22, 1987, abandoned, which is a continuation of Ser. No. 764,393, Aug. 12, 1985, abandoned.

[51] Int. Cl.$^5$ .................................................. C12P 7/06
[52] U.S. Cl. ................................... 435/161; 435/162; 435/163; 435/164; 435/165; 435/157; 435/813

[58] Field of Search ............... 435/157, 813, 161, 163, 435/164, 162, 165; 568/913, 916, 918; 203/19, DIG. 13

[56] References Cited

U.S. PATENT DOCUMENTS 2,139,179 12/1938 Tulleners ........................... 568/918
4,409,406 10/1983 Feldman ........................... 568/916

*Primary Examiner*—Douglas W. Robinson
*Assistant Examiner*—Marian C. Knode
*Attorney, Agent, or Firm*—Deveau, Colton & Marquis

[57] ABSTRACT

A process for recovering alcohol by a continuous process employing fermentation, solvent extraction of the alcohol product, extractive distillation of the alcohol-solvent extract to provide water fraction and vacuum stripping for separation of the alcohol and regenerated solvent.

The solvent is recycled. An isoparaffin is used as a solvent and this solvent can be modified with a long chain fatty acid, alcohol or fatty alcohol or long-chain esters. Alternatively, many modifiers may be used neat.

32 Claims, 4 Drawing Sheets

PROCESS FOR RECOVERING ALCOHOL WITH ENERGY INTEGRATION

CROSS-REFERENCE TO RELATED APPLICATION

This is a continuation-in-part of my prior co-pending application Ser. No. 07/298,216 filed Jan. 17, 1989, now U.S. Pat. No. 5,036,005, which is a continuation-in-part of my prior co-pending application Ser. No. 07/054,037 filed May 22, 1987, now abandoned, which is a continuation of my prior co-pending application Ser. No. 06/764,393 filed Aug. 12, 1985, now abandoned.

BACKGROUND OF THE INVENTION

1. Field of the Invention

This invention relates to a continuous process for producing alcohol and is more particularly concerned with a continuous process of producing alcohol through continuous fermentation, solvent extraction, extractive distillation dehydration and vacuum stripping.

2. Description of the Prior Art

The old method of separating alcohols from water uses distillation. Typically, a beer still is used to process the fermented product which contains alcohol in an aqueous mixture and thereby produces an enriched alcohol mixture which is then dried using azeotropic distillation. Solvent extraction processes have been developed earlier, but these systems do not enable the recovery of ethanol which is dry enough to produce gasohol in a single distillation step. My present invention, using extractive distillation dehydration followed by vacuum stripping, appears to be superior to the earlier solvent regeneration techniques in that it reduces the energy requirement further and produces a higher quality product.

SUMMARY OF THE INVENTION

Briefly described, the present invention provides a continuous process for recovering low molecular weight carboxylic acids and alcohols from dilute aqueous mixtures typically produced by fermentation. In the process, the alcohol, typically ethanol, is generated continuously, being produced from molasses, fermentation microorganisms and water in a fermentation tank. The fermenter product or beer or broth produced is continuously fed to a solvent extraction column where a solvent dissolves the alcohol and other low molecular weight metabolites (e.g., acetic and lactic acids) to produce an extract which is immiscible in water, but contains the bulk of the inhibitory metabolites. For enhanced alcohol recover from the process, the fermenter product or beer or broth produced may be preheated prior to being fed to the solvent extraction column. The raffinate therefrom, containing water, residual alcohol fermentation microorganisms, and solids may then be recycled via a decanter and, optionally, an evaporator and filter system. The liquid effluent may then be returned to the fermentation tank. The extract from the liquid/liquid extraction column passes, via a decanter and heat exchangers, to an extractive distillation dehydration unit for extractive distillation which separates, as an overhead, the water from the alcohol and solvent. The dehydrated extract (alcohol and solvent), is then fed to a vacuum stripper, where the fuel grade alcohol is separated from the solvent. In case other inhibitory metabolites (e.g., acetic acid) are present these may also be recovered at this point. The solvent portion from the vacuum stripper is then returned to the solvent extraction and extractive distillation columns.

Significant parts of this invention are the improved solvent regeneration steps which are associated with the ethanol and other alcohol extractions. In my earlier inventions, solvent regeneration has been based upon either vacuum stripping or carrier gas stripping of the extract. This invention improves on the earlier inventions by enabling the recovery of fuel grade ethanol without the use of a second solvent. Also, the extractive distillation step is used to selectively dry the solvent, and it is followed by the recovery of the dry ethanol in a vacuum stripping step.

DESCRIPTION OF THE PREFERRED EMBODIMENT

Figure 1:
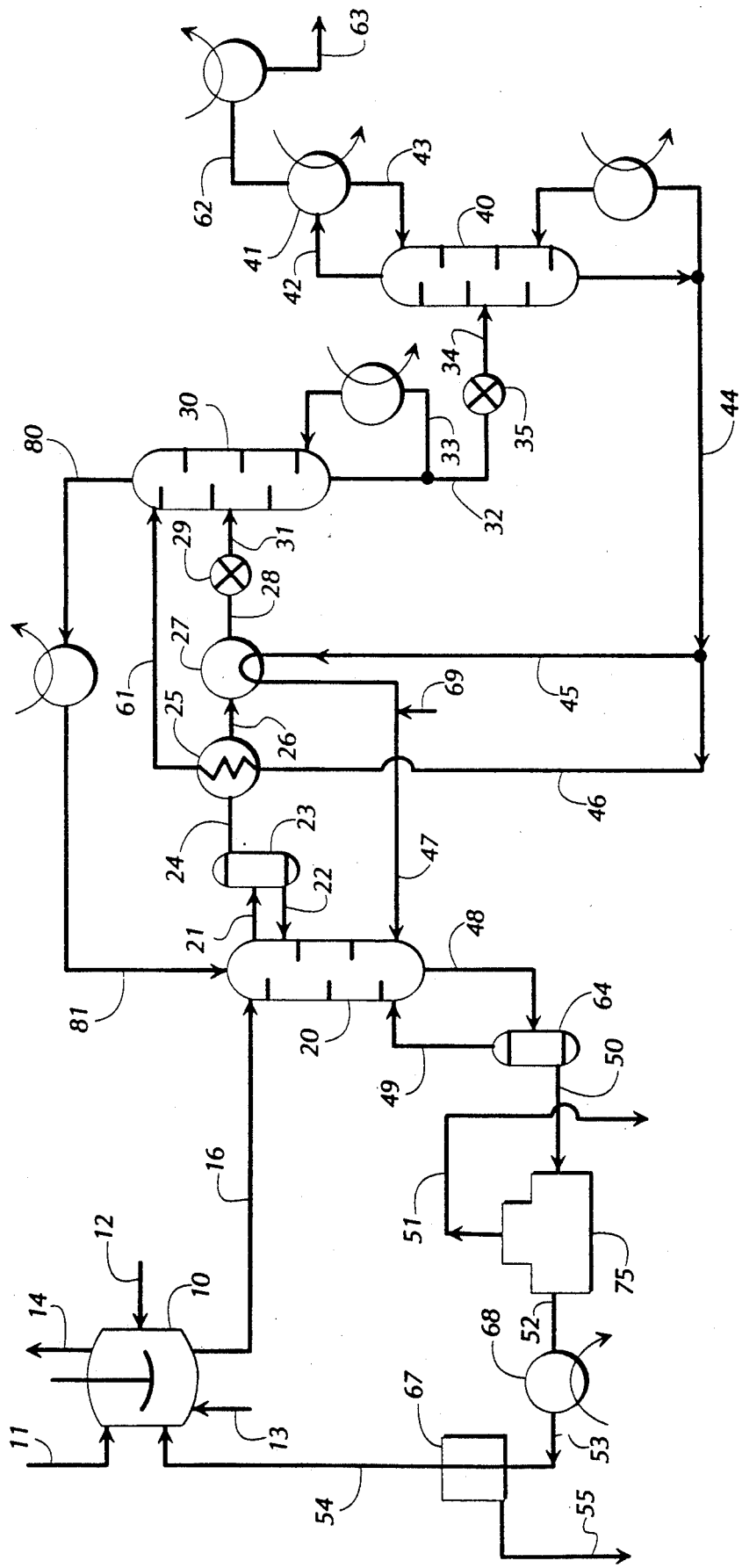
FIG. 1 is a flow diagram of the process of the present invention.

Referring now in detail to the embodiment chosen for the purpose of illustrating the best mode of the present invention as shown in FIG. 1 numeral 10 denotes a conventional fermenter or fermentation tank or vat in which a concentrated aqueous solution of molasses containing sugar is fermented using brewers' yeast or another fermentation microorganism or microbe such as *Saccharomyces cerevisiae* for converting the sugars and starches into alcohol, namely, ethanol.

The concentrated aqueous solution of molasses, with sugar therein, used as the feed material is fed to the fermenter 10, either intermittently or continuously, via pipe 11, and the fermentation microorganisms, such as brewers' yeast in a water carrier, are fed, as needed, via pipe 12, to tank 10. Air for sparging is introduced, via pipe 13, and the "off gases", namely the excess air and carbon dioxide are discharged, via duct 14. The fermenter product, namely the beer or broth from the fermentation tank 10 is fed, via pipe 16, to the solvent extraction column or unit 20 wherein an organic solvent for the alcohol is admixed with the fermenter product. The fermenter 10 is operated continuously to produce this fermenter product which is sent to the solvent extraction column 20. The alcohol concentration is generally between 5-10%, however, the microorganisms used for the fermentation can tolerate alcohol concentrations up to about 15%. The process of the present invention has also been found to be effective in recovering alcohol from dilute fermenter products having about 0.5-5.0% alcohol.

In the solvent extraction column 20, a water distillate product, stream 81, from the extractive dehydration step is combined with this fermenter product, as the product is added to the solvent extraction column 20. The fermenter product, stream 16, may be introduced as an intermediate feed to the solvent extraction column 20 while the water distillate product from the extractive distillation dehydration is added, as a scrub, to the solvent extraction column 20. This permits efficient liquid/liquid extraction of the ethanol from the fermenter product or broth or beer, at reduced costs.

Maintaining a high sugar concentration of about 3% by weight in the fermenter 10 and in the feed, i.e., in the fermenter product, that is sent to the solvent extraction column 20, favorably enhances the ability of the solvent extraction column 20 selectively to extract ethanol. Fermenter 10 and extraction column 20 are maintained at approximately 27° C., and can be as low as 23° C. Two effects are noted: (1) the ethanol exhibits higher distribution coefficients in the presence of sugar; and (2) the water activity is reduced and, therefore, less water is co-extracted into the solvent extract.

The extract from the solvent extraction column 20, which contains the alcohol, the solvent or solvents, residual water and foam solids, is then sent to an extractive distillation dehydration unit 30. In its travel from the liquid-to-liquid extraction column 20 the dehydration unit 30, the extract, which is made up mostly of alcohol and solvent, passes, via pipe 21, to a gravity separator, such as decanter 23, wherein the heavier fraction, usually containing water, microorganisms and solids, is returned, via pipe 22 to an intermediate portion of the column 20.

Extractive distillation, unit 30, is operated so as to partially strip the extract. Because the water which is co-extracted with the ethanol can be selectively stripped using extractive distillation, I am able to effectively dehydrate the extract and produce a fuel grade product in a single cycle. A key feature of the extractive distillation, unit 30, is the ability to effectively dehydrate the extract without distilling a significant portion of the solvent. This is accomplished by sending regenerated solvent, stream 61, to the top of the extractive distillation column but without evaporating large amounts of solvent. Hence the energy requirements are very low.

It is important to note that the volatility of water is much greater than that of ethanol in the presence of the solvent. This means that the extractive distillation column requires very few actual stages compared to equivalent distillation. For example, in the laboratory we have been able to maintain ethanol concentrations less than 1 wt % in stream 80 simply by adjusting the conditions (flowrates and temperatures) of streams 61 and 31. In these tests, column 30 contained only 3 bubble cap trays between streams 31 and 61 and only 3 bubble cap trays between streams 31 and 32 or only 6 actual trays in all which is much less than for distillation. However, we often prefer to control stream 80 at about 10 wt % ethanol. The heat exchangers 25 and 27 serve as preheaters for the dehydration unit 30 which in order to dry efficiently and quickly should be maintained at about 85° C. Drying temperatures up to about 150° C. have been used effectively.

In the extractive distillation dehydration unit 30, the water ethanol mixture forms an overhead which is removed from the extractive distillation unit 30 and is recycled back to the solvent extraction system. In general, it is desirable to maintain low ethanol concentrations in this stream, but any ethanol which may be present is not lost since it is recycled to solvent extraction, unit 20. The bottom effluent from the extractive distillation unit is a dehydrated extract which contains the bulk of the solvent and ethanol, but only very small quantities of water. It also contains any co-extracted acids (e.g., acetic acid).

From the dehydration unit 30, the dehydrated extract is sent, via pipe 32, valve 35 and pipe 34 into a vacuum stripping unit 40 for ethanol removal and solvent regeneration. In order to control solvent carry-over, some refluxing of the resulting ethanol is necessary, but these requirements are relatively small. For refluxing, I have provided partial condenser 41 to which the overhead (primarily alcohol) from unit 40 is fed, as illustrated, through line 42, the return of the solvent being by line 43.

In actual practice, the amount of solvent carried over in stream 43 can be kept very small. It depends upon the solvent mixture used, the number of trays in column 40 and the temperature at the bottom of column 40. In the lab, for example, we have kept solvent carryover (stream 43) to less than one (1)% of the total condensed product (stream 63) by simply avoiding, excessive heating at the bottom of the column stream 40 and the pressure drop between the columns (streams 32 and 34). In this test, column 40 contained very few actual bubble cap trays (only 2 between streams 43 and 34 and only 4 between streams 34 and 44). Because of the prior extractive distillation dehydration, the ethanol product or extract, which is discharged as the final product, is much drier than can be obtained if the produce is stripped without the extractive distillation step. This overhead product, which is discharged through pipe 46, is fuel grade alcohol (98%+ alcohol).

The preheater or first heat exchanger 25, which is in series with second heat exchanger 27, in the alcohol extract line between the solvent extraction unit 20 and the dehydration unit 30 are heated by the hot regenerated solvent. This regenerated solvent is then fed to the solvent extraction column or unit 20, via pipe 47 or to the extractive distillation column, stream 61. Make up solvent can be conveniently introduced, via pipe 69, into pipe 47. In actual practice, however, virtually no solvent makeup is required because (1) the aqueous solubility of the solvent is very low and (2) the volatility of the solvent is quite low compared to the extracted water, ethanol and any other metabolites. In the laboratory we have demonstrated essentially 100% solvent recycle because of these low losses and no measurable solvent degradation during recycle.

With respect to column 20, the bottom raffinate, which contains the microorganisms, the solids and the water, together with residual amounts of solvent, is recycled, via pipe 48, decanter or separator 64, evaporator 75, heat exchanger 68, filter 67, and pipes 52, 53 and 54 and sent to the fermenter 10. In the decanter 64, any entrained solvent is removed, via pipe 49 and returned to unit 20.

The evaporator 75 (optional) may be used to remove excess water. However, a bleed stream may also be used to accomplish the same purpose. In case an enzyme of importance is in the fermentate, this latter option may be preferred. Heat exchanger 68 is used to return the recycle stream to the temperature of the fermenter, unit 10. Finally, excess or degraded biomass may be removed via filter 67. In some cases, metal ion removal may also be desirable depending upon the substrate which is being fermented.

The advantages of this process are significantly reduced energy and capital costs and the elimination of secondary waste production during the solvent regeneration step. Other techniques require substantially more energy due to higher reflux requirements. Also, other techniques require more capital investment due to lower fermenter productivities and significantly greater tray requirements (i.e., much taller columns as in distillation). Thirdly, the concept appears to be an improvement over the process of using two solvent extraction cycles because it avoids the solvent cross-contamination problems which would be existing with this concept.

Standard equipment items may be used for the liquid/liquid extraction column 20, extractive distillation dehydration unit 30, and vacuum stripping unit 40. Standard equipment can also be used for the continuous fermentation, fermenter 10. This technology is well developed and a number of equipment items may be used effectively; however, it is preferred to use a solvent extraction column which is relatively gentle on the microorganisms which pass through it. Specifically, it would be undesirable to use a high speed centrifugal contactor to achieve the solvent extraction step. A preferred equipment item would be the rotating disc column or the reciprocating plate column for solvent extraction or mixer-settlers.

Pressure ranges throughout the system vary anywhere from 100 mmHg to 760 mmHg. Solvent regeneration is best accomplished at about 100 mmHg or greater in order to use cooling water to condense the product rather than refrigeration.

The preferred solvents for the present invention consist of branched paraffin diluents ranging from $C_{12}$ to $C_{16}$, such as ISOPAR-L or ISOPAR-M and the like which are isoparaffin diluents also include substances, such as NORPAR-12 or NORPAR-13 which are linear alkanes composed primarily of $C_{11}$ and $C_{12}$ hydrocarbons. The branched paraffins, like ISOPAR-L or ISOPAR-M, are preferred due to their higher selectivity from branching.

The selected solvent need not be limited to the above-mentioned preferred solvents. The solvent used in the present invention must not be toxic to fermentation microorganisms. Water must be more volatile than ethanol in the presence of the selected solvent and the solvent should be less volatile than either water or ethanol in ternary mixtures of these three species. The solvent must not form stable emulsions when mixed vigorously with fermentation broths. The solvent should be chemically stable in the presence of fermentation broths or, if it undergoes degradation, the degradation products must exhibit similar properties as the solvent. The solvent must be a liquid at all operating temperatures in the process. The solvent must not be highly flammable or result in explosive conditions within the process. The solvent viscosity, density, and liquid/liquid interfacial tension with fermentation broths must be such as to enable a primary break time of less than ten minutes. If the solvent includes nonpolar diluents, then extracts should not form third phases.

The selected solvent must include chemical groups which enable it to coordinate and solvate ethanol. In addition to those species already cited, the solvent could include hydroxydiols, polysilicates, or other similar polar functionalities that enable hydrogen bonding and/or solvation coordination with ethanol.

The preferred diluents may be suitably modified with substances, such as tridecyl alcohol, tridecyl acid, tridecyl acetate, and the like or tri-n-butyl phosphate which are blended in the solvent, i.e., diluent. The above modifiers are preferred over solvents, such as 2-ethyl hexanol or octanol, because these latter alcohols exhibit a higher toxicity to microorganisms. The preferred solvents on the other hand exhibit negligible toxicity to microorganisms such as brewers' yeast.

Laboratory tests have shown, for example, that my solvents have no toxic effects on microbe viability for the following species: *Saccharomyces cerevisiae*. *Thermoanaerobacter ethanolicus*, *Clostridium thermocellum*. or *Zymomonis mobilis*. Insofar as the solvents have no effect on *Zymomonis Mobilis* (a particularly sensitive microbe), I believe they will not affect any microbe of interest.

In fact, the reason these solvents have no effect proves another important solvent benefit. Namely, the aqueous solubilities of my recommended solvents are exceedingly small. Hence, the solvents do not interfere with microbe functions in any way yet they are useful for metabolite removal.

As is well known, other by-products are produced during fermentation besides alcohol. These include acetic and lactic acids, both of which do extract to some extent in the solvents. However, I do not recommend tri-n-butyl phosphate (TBP) as a solvent whenever the pH of the fermentate is low and significant acids are co-extracted. During runs with tri-n-butyl phosphate (TBP), it was observed that some solvent degradation appears to occur with this phosphate ester. Batch tests were conducted by heating a sample of the solvent with the beer to temperatures around 80° C. Subsequently, it was observed that the organic phase darkened visibly. This observation suggests that solvent degradation will be a problem if this ester is used. On the other hand, tridecyl acetate is an ester which may be highly suitable, especially if one extracts from beers containing significant acetate concentrations.

In other cases, it is often preferable to use the branched chain paraffins as solvents and/or chain alcohols, such as tridecyl alcohol and decyl alcohol which do not experience this degradation problem. The appropriate ratio of solvent to alcohol is approximately 1:1. However, solvent to alcohol ratios as high as 10 to 1 or a low as 1 to 10 may also be preferred for certain applications. Alternatively, the solvent may consist of 100% modifier (e.g., tridecyl alcohol). This solvent has been used successfully on very dilute fermentates, for example.

Long-chain alcohols and acids are suitable modifiers for paraffin and/or alcohol solvent systems. Fatty alcohols and fatty acids are also useful as solvents. Some examples of fatty alcohols which are useful solvents include lauryl, cetearyl, cetyl, stearyl, and tallow types. Fatty acids which are useful as solvents include coconut, tallow, and linseed fractions. These alcohols and acids are relatively inexpensive. Chemically the alcohols are very similar to tridecyl alcohol although they often contain longer aliphatic chain groups on them.

The coupling of solvent extraction with continuous fermentation offers the possibility of higher alcohol production rates with reduced costs. There is also a favorable interaction between solvent extraction and continuous fermentation since the solvents which I suggest exhibit low toxicity. The use of lower molecular weight alcohols, such as octanol, are unacceptable for this application because of their toxicity to the microorganisms in the fermenter.

The solvent extraction process is enhanced substantially by the presence of sugar in the fermentation effluent. It would be desirable to operate the fermenter at the highest possible sugar concentration, although there are some problems with this mode of operation since high sugar concentrations can also inhibit the fermentation process. However, maintaining the sugar concentration in the fermenter at approximately 3% by weight results in a product having a sufficiently high sugar concentration in the effluent. The pH range is not that critical except that the fermentation should be carried out in a slightly acidic environment in order to prevent the formation of stable emulsions.

Another advantage of the continuous fermenter and solvent extraction equipment, especially if a reciprocating plate column is used, is that it eliminates the need to remove the biomass from the fermenter product. This advantage eliminates the use of a centrifuge which is relatively expensive. In this case, filter 67 is also not used. However, it does limit the type of contactor which can be used in the solvent extraction step. Specifically, it is necessary to use a contactor which mixes the two phases with relatively low shear stress, otherwise the cell viability is reduced.

There is a favorable interaction between the extractive distillation unit 30 and the solvent extraction unit 20. Specifically, the presence of the extractive distillation allows the use of less selective solvents in unit 20 which have greater solute capacities and distribution coefficients. Hence, the restrictions concerning loss of selectivity with increased ethanol concentrations are eliminated by this synergism. Moreover, this problem is more difficult to overcome using other techniques.

There is an interaction between the extractive distillation dehydration unit 30 and the vacuum stripping unit 40 which is favorable. Specifically, the elimination of the extractive distillation dehydration unit 30 does not permit the recovery of fuel grade ethanol in a single extraction cycle. However, the dehydration unit 20 removes that water which is present in the extract and, therefore, the ethanol product can be taken during the vacuum stripping step to produce a high quality product.

The process described above is superior to ethanol recovery by membrane permeation since membranes are susceptible to fouling. Also, membranes are relatively expensive. Also, the current invention utilizes relatively simple unit operations which can be easily scaled up to commercial size.

Although I have not completed a detailed evaluation of the above process, it appears that it will permit further reductions in energy use compared to earlier inventions. Specifically, this process will enable recovery of fuel grade product by distilling the ethanol product only once. The earlier concepts, particularly the two cycle process, require that the ethanol product be evaporated and condensed twice. In the present concept this difficulty is avoided and, therefore, it is expected that it will offer the most efficient method for recovering fuel grade ethanol directly.

When this invention (unoptimized) is compared to optimized distillation, significant savings in recovery costs become apparent. These savings are also a function of the solute (ethanol) concentration in the fermentate and they are larger as the fermentate quality decreases. For example, a manufacturer producing 100 million liters per year of 99+ ethanol (99% recovery) will realize a net savings of about 10¢ per gallon of ethanol if the fermentate contains about 5 weight to percent ethanol. If the fermentate contains about 1.9 weight to percent ethanol, my invention will save at least 30¢ per gallon recovered. If the fermentate contains about 0.6 weight to percent ethanol, my invention will save at least 40¢ per gallon. Higher savings will probably be realized; however, since my invention has not yet been completely optimized. Clearly, however, this invention is highly valuable for ethanol recovery from low grade fermentates such as from waste materials.

ENHANCED RECOVERY

Figure 2:
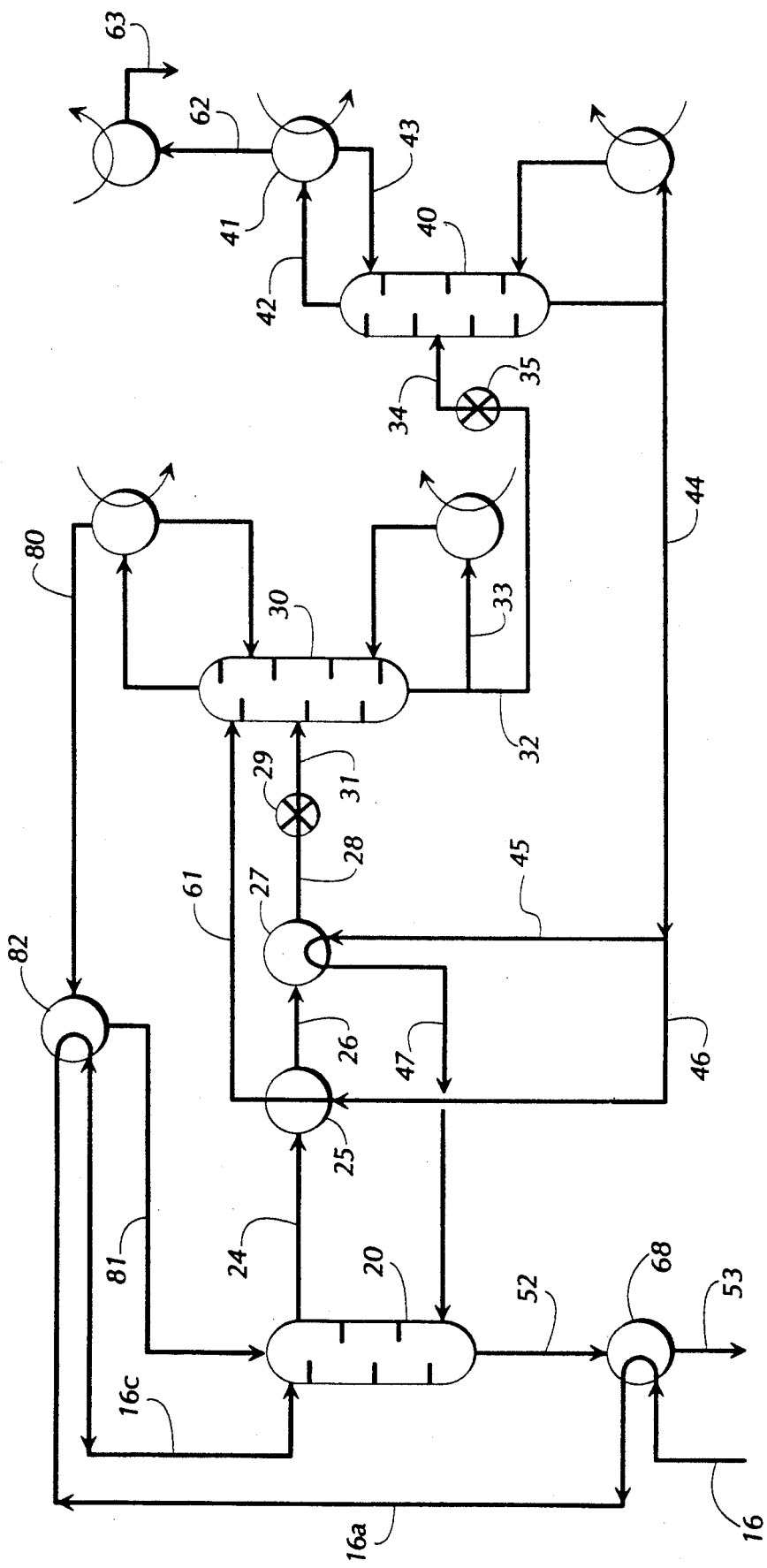
FIG. 2 is a flow diagram of a first alternate embodiment of the process of the present invention resulting in enhanced recovery.
Figure 3:
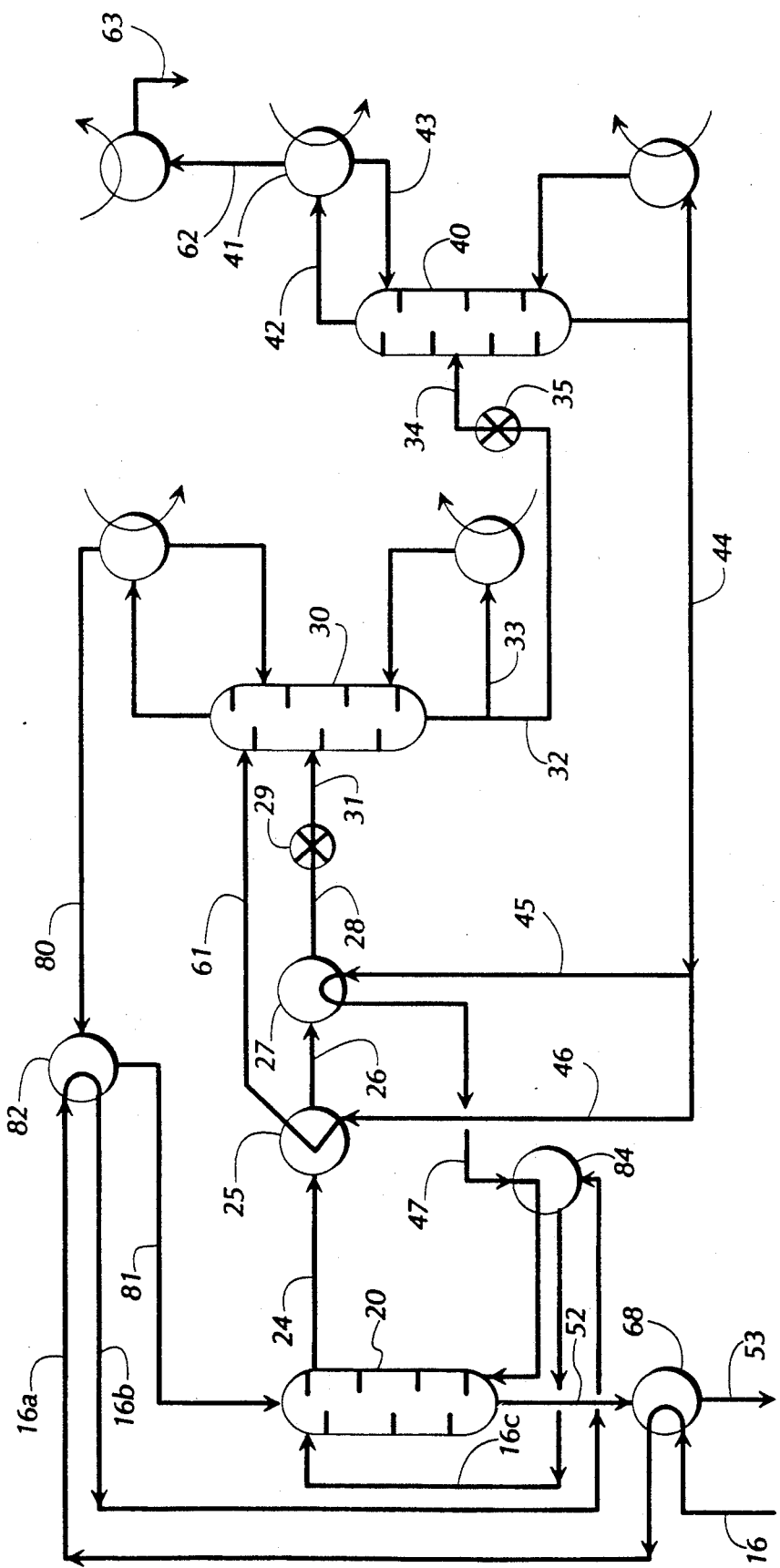
FIG. 3 is a flow diagram of a second alternate embodiment of the process of the present invention also resulting in enhanced recovery.
Figure 4:
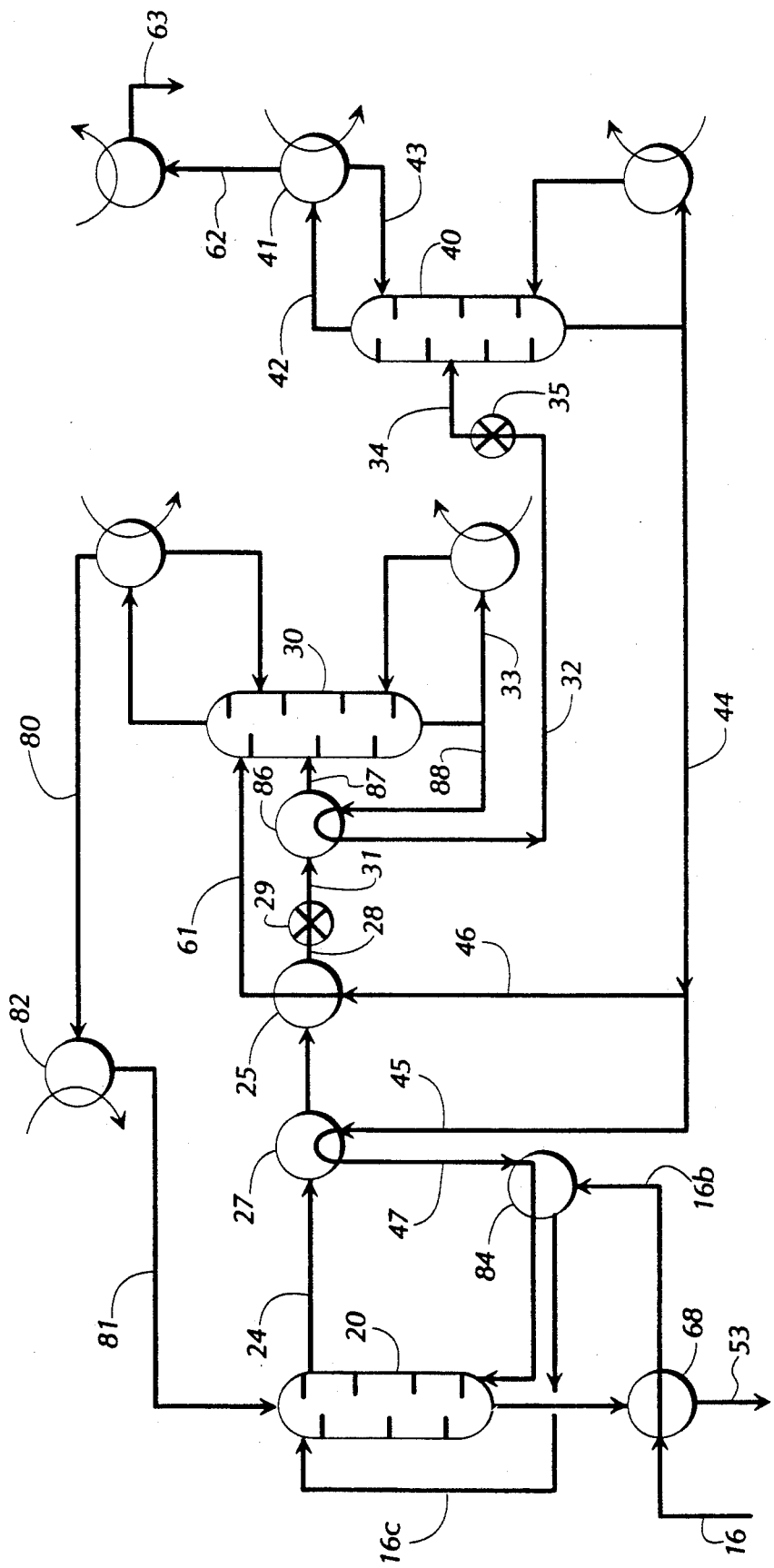
FIG. 4 is a flow diagram of a third alternate embodiment of the process of the present invention also resulting in enhanced recovery.

An enhanced recovery of alcohol from the process can be accomplished by preheating the fermenter product, namely the beer or broth, from the fermentation tank 10 prior to introducing the fermenter product to the solvent extraction column or unit 20. This can be best accomplished by the addition of a heat exchanger or a plurality of heat exchangers along pipe 16. As shown in FIGS. 2, 3, and 4, the use of heat exchangers 68, 82, and 84 is contemplated. Heat exchanger 68 shown in FIGS. 2, 3, and 4 corresponds to heat exchanger 68 shown in FIG. 1; heat exchanger 82 shown in FIGS. 2, 3, and 4 corresponds to the heat exchanger located between streams 80 and 81 shown in FIG. 1; and heat exchanger 84 is an addition to the enhanced recovery embodiments to the process.

As in the general process disclosed above, the enhanced recovery processes diagrammed in FIGS. 2, 3, and 4 act on a fermenter product resulting from the fermentation of a concentrated aqueous solution of molasses containing sugar using brewers' yeast or another fermentation microorganism or microbe for converting the sugars and starches into alcohol, namely, ethanol. The concentrated aqueous solution and the fermentation microorganisms are fed to the fermenter, such as fermenter 10 in FIG. 1.

In the first alternative process, shown in FIG. 2, the fermenter product from the fermentation tank is passed through, via pipe 16, heat exchanger 68 where the fermenter product is preheated by the bottom raffinate from solvent extraction column 20. The preheated fermenter product then is passed through, via pipe 16a, heat exchanger 82 where the preheated fermenter product is further preheated by the water distillate product, stream 81, from the extractive distillation dehydration unit 30. The further preheated fermenter product then is fed, via pipe 16c, to the solvent extraction column or unit 20. From this step on, the fermenter product is processed as disclosed in the primary embodiment above.

In the second alternative process, shown in FIG. 3, the fermenter product from the fermentation tank is passed through, via pipe 16, heat exchanger 68 where the fermenter product is preheated by the bottom raffinate from solvent extraction column 20. The preheated fermenter product then is passed through, via pipe 16a, heat exchanger 82 where the preheated fermenter product is further preheated by the water distillate product, stream 81, from the extractive distillation dehydration unit 30. The further preheated fermenter product then is passed through, via pipe 16b, heat exchanger 84, which has been added to pipe 47, where the further preheated fermenter product is still further preheated by the bottom raffinate from the volume stripping unit 40. The still further preheated fermenter product then is fed, via pipe 16c, to the solvent extraction column or unit 20. From this step on, the fermenter product is processed as disclosed in the primary embodiment above.

In the third alternative process, shown in FIG. 4, the fermenter product from the fermentation tank is passed through, via pipe 16, heat exchanger 68 where the fermenter product is preheated by the bottom raffinate from solvent extraction column 20. The preheated fermenter product then is passed through, via pipe 16b, heat exchanger 84 which has been added to pipe 47, where the further preheated fermenter product is still further preheated by the bottom raffinate from the vacuum stripping unit 40. The still further preheated fermenter product then is fed, via pipe 16c, to the solvent extraction column or unit 20. From this step on, the fermenter product is processed as disclosed in the primary embodiment above.

FIG. 4 also shows an optional preheating step for the extractive distillation dehydration unit 30 raffinate prior to extractive distillation dehydration unit raffinate being fed to the vacuum stripping unit 40. Extractive distillation dehydration unit raffinate is passed through, via pipe 88, heat exchanger 86, which has been added to pipe 31, where the extractive distillation dehydration unit raffinate is preheated by the extract from the solvent extraction unit 20. The preheated extractive distillation unit raffinate then is fed, via pipe 32, to the vacuum stripping unit 40.

Using the enhanced recovery processes disclosed above, heat is introduced into the beer stripper and passed to the beer concentrator by matching the stripper condenser with the concentrator reboiler. Hence, the concentrator operates at reduced pressures. By heat exchanger matching, the energy requirements for the azeotropic distillation are satisfied from the stripper duty. The enhanced recovery processes result in higher alcohol yields with reduces costs due to lower solvent extraction energy requirements and lower cooling water requirements when compared to optimized distillation.

The enhanced recovery processes offer new opportunities for heat exchanger matching and facilitate beer preheating with significantly reduced transfer area requirements. Cost analysis for the enhanced recovery processes suggest that solvent extraction becomes more economically attractive as the beer quality decreases. Capital investment requirements are also less than for optimized distillation, especially for lower grade beers.

It will be obvious to those skilled in the art that many variations may be made in the embodiment here chosen for the purpose of illustration without departing from the scope thereof, as defined by the appended claims.

I claim:

1. A process of producing alcohol comprising:
   (a) feeding a sugar and water containing feed stock to a fermenter;
   (b) providing the fermenter with fermentation microorganisms and operating the fermenter continuously for converting the feed stock into a fermentation product containing alcohol, sugar and microorganisms;
   (c) preheating said fermentation product;
   (d) feeding said fermentation product to a solvent extraction column;
   (e) delivering to said solvent extraction column a solvent which is non-toxic to the fermentation microorganisms and which will dissolve and decrease the volatility of said alcohol relative to the water in said feedstock such that said water is more volatile than said alcohol in the presence of said solvent and said solvent is less volatile than either said water or said alcohol in ternary mixtures of said solvent, said water and said alcohol, said solvent is immiscible in the water in the fermentation product for liquid to liquid extraction of the alcohol for providing an alcohol-solvent extract phase and a water phase, said water phase comprising microorganisms, solids and water;
   (f) removing alcohol-solvent extract phase from said solvent extraction column and directing the alcohol-solvent extract phase to an extractive distillation dehydration unit;
   (g) removing said water phase from said solvent extraction column and returning said water phase to said fermenter;
   (h) distilling in said extractive distillation dehydration unit the bulk of the residual water from said alcohol-solvent extract phase leaving a dehydrated extract including alcohol and solvent to provide more efficient liquid/liquid extraction of the alcohol from the fermentation product in said solvent extraction column;
   (i) returning the distilled water from said extractive distillation dehydration unit to the solvent extraction column;
   (j) delivering said dehydrated extract to a vacuum stripping unit;
   (k) separating said alcohol from said solvent in said dehydrated extract in said vacuum stripping unit to produce regenerated solvent and alcohol product;
   (l) returning a portion of the regenerated solvent to said extractive distillation dehydration unit and a portion of the regenerated solvent to said solvent extraction column; and
   (m) discharging said alcohol product from said vacuum stripping unit.

2. The process defined in claim 1, further comprising decanting said water phase after said water phase has been removed from said solvent extraction column and prior to recycling said water phase into said fermenter.

3. The process defined in claim 1 wherein the solvent which is returned to said solvent extraction column is fed to a decanter prior to being delivered to said solvent extraction column and delivering the overflow of said solvent from said decanter to the extractive distillation dehydration unit.

4. The process defined in claim 1 further comprising preheating said dehydrated extract during said delivering of said dehydrated extract form said extractive distillation dehydration unit to said vacuum stripper.

5. The process defined in claim 1 further comprising condensing said alcohol product prior to discharging said alcohol product from said vacuum stripper.

6. The process defined in claim 1 further comprising adding makeup solvent to said solvent extraction column.

7. The process defined in claim 1 wherein said solvent comprises a branched chain paraffin.

8. The process defined in claim 1 wherein said solvent is selected from the group consisting of branched chain paraffins, linear chain paraffins, long chain fatty acids, long chain alcohols, long chain fatty alcohols, and long-chain esters.

9. The process defined in claim 7 wherein said solvent further comprises a compound selected from the group consisting of tridecyl alcohol, decyl alcohol, fatty alcohols, long-chain alcohols, fatty acids, and long-chain esters.

10. The process of claim 9 wherein said solvent comprises equal parts of said branched chain paraffin and said compound.

11. The process of claim 1 wherein the sugar concentration in said fermenter is about 3% by weight.

12. The process of claim 1 wherein the alcohol concentration in the fermentation product ranges from 0.5 to 15.0%.

13. The process of claim 1 wherein the alcohol concentration in the fermentation product is approximately 5-10%.

14. The process of claim 1 wherein said solvent is present in a ratio to said alcohol in step (e) of from 10/1 to 1/10.

15. The process of claim 14 wherein said solvent is a blend of long-chain esters mixed with long chain alcohols.

16. The process of claim 1, wherein said solvent comprises blended solvents and further comprises the step of recovering metabolites from the solvent extract.

17. The process of claim 16, wherein said blended solvents are used to co-extract metabolites simultaneously and recover them as dehydrated species.

18. The process of claim 1, wherein the solvent is selected from the group consisting of undiluted alcohol, tridecyl acetate, and tridecyl acid.

19. The process of claim 1 wherein said solvent comprises hydroxydiols, polysilicates, or other similar polar functionalities that enable hydrogen bonding and/or solvation coordination with said alcohol.

20. The process of claim 1, wherein said solvent has a viscosity, density, and liquid/liquid interfacial tension with said fermentation product that there is a primary break time of less than ten minutes.

21. The process of claim 1, wherein the distilled water returned to the solvent extraction column comprises alcohol produced in step (b).

22. The process of claim 1, further comprising the step of separating a heavier fraction containing water from the alcohol-solvent extract phase removed from the solvent extraction column before directing said alcohol-solvent extract phase to the extractive distillation dehydration unit.

23. The process of claim 1, wherein the fermentation product is preheated by heat exchange with the bottom raffinate from said solvent extraction column.

24. The process of claim 23, wherein the fermentation product is further preheated by heat exchange with the top distillate from said extractive distillation dehydration unit.

25. The process of claim 24, wherein the fermentation product is further preheated by heat exchange with the bottom raffinate from said vacuum stripping unit.

26. The process of claim 23, wherein the fermentation product is further preheated by heat exchange with the bottom raffinate from said vacuum stripping unit.

27. The process of claim 1, wherein the fermentation product is preheated by heat exchange with the top distillate from said extractive distillation dehydration unit.

28. The process of claim 27 wherein the fermentation product is further preheated by heat exchange with the bottom raffinate from said vacuum stripping unit.

29. The process of claim 1, wherein the fermentation product is preheated by heat exchange with the bottom raffinate from said vacuum stripping unit.

30. The process of claims 23, 24, 25, 26, 27, 28, or 29, wherein the bottom raffinate from said extractive distillation dehydration unit is preheated by heat exchange with the alcohol-solvent extract phase.

31. A process for recovering alcohol from a fermentation product containing alcohol, sugar, water and microorganisms, comprising preheating said fermentation product, contacting said fermentation product countercurrently with a solvent having low microbial toxicity which is miscible with said alcohol and will decrease the volatility of said alcohol relative to said water such that the volatility of the alcohol in the presence of solvent is less than that of said water, said solvent containing a paraffin selected from the group consisting of branched and linear alkanes having $C_{12}$ to $C_{16}$ for providing an alcohol solvent phase and a water phase, separating the alcohol-solvent phase from the water phase, adding regenerated solvent to said alcohol-solvent phase, distilling the residual water from the alcohol-solvent phase, recycling said distilled water to the step in the process where said fermentation product is contacted with said solvent, 32. The process defined in claim 31 wherein the solvent comprises a hydrocarbon selected from the group consisting of fatty alcohols, fatty acids, long chain alcohols, and long-chain esters.

* * * * *